US006455760B1

(12) United States Patent
Zhao et al.

(10) Patent No.: US 6,455,760 B1
(45) Date of Patent: Sep. 24, 2002

(54) EXPRESSION OF FLAVIN-CONTAINING MONOXYGENASES IN PLANTS

(75) Inventors: Yunde Zhao, San Diego; Joanne Chory, Del Mar, both of CA (US); Christian Fankhauser, Onex (CH); Detlef Weigel, Solana Beach; John Cashman, San Diego, both of CA (US)

(73) Assignee: The Salk Institute of Biological Studies, La Jolla, CA (US)

( * ) Notice: Subject to any disclaimer, the term of this patent is extended or adjusted under 35 U.S.C. 154(b) by 0 days.

(21) Appl. No.: 09/715,834

(22) Filed: Nov. 16, 2000

(51) Int. Cl.$^7$ .......................... A01H 5/00; C12N 15/82; C07H 21/04
(52) U.S. Cl. ...................... 800/290; 800/298; 435/410; 435/419; 435/468; 536/23.6; 536/23.1
(58) Field of Search ................................. 800/290, 294, 800/298, 278; 536/23.6, 23.1; 435/468, 419, 410

(56) References Cited

PUBLICATIONS

Zhao et al, "A role for flavin Monooxygenase–Like Enzymes in Auxin Biosynthesis", Jan. 2001, Science vol. 291, pp. 306–309.*
Janssen et al, "Overexpression of a Homeobox Gene, LeT6 Reveals Indeterminate Features in the Tomato Compound Leaf", 1998, Plant Physiol. vol. 117, pp. 771–786.*
Vollbrecht et al, "The developmental gene Knotted–1 is a member of a maize homeobox gene family", Mar. 1991, Nature vol. 350, pp. 241–243.*

Boerjan, et al., superrot, a Recessive Mutation in Arabidopsis, Confers Auxin Overproduction; The Plant Cell, vol. 7:1405–19. (1995).
Cashman, et al., Population–Specific Polymorphisms of the Human FM03 Gene: Significance for Detoxication; Drug Metabolism and Disposition. vol. 28(2):169–173.
Delarue, et al., Sur2 mutations of *Arabidopsis thailiana* define a new locus involved in the control of auxin homeostasis; The Plant Journal. 14(5):603–611 (1998).
Hooley, et al., Auxin Signaling: Homing in with Targeted Genetics; the Plant Cell. vol. 10:1581 (1998).
Lehman, et al., HOOKLESS1, an Ethylene Response Gene, Is Required for Differential Cell Elongation in the Arabidopsis Hypocotyl; *Cell*, vol. 85, 183–194 (1996).
Leyser, et al., Arabidopsis auxin–resistance gene AXR1 encodes a protein related to ubiquitin–activating enzyme E1; Nature. vol. 364:161–64 (1993).
King, et al., A Mutation Altering Auxin Homeostasis and Plant Morphology in Arabidopsis; The Plant Cell. vol. 7:2023–37 (1995).
Ruegger, et al. The TIR1 protein of Arabidopsis functions in auxin response and is related to human SKP2 and yeast Grr1p;; Genes & Development. 12:198–207 (1998).

* cited by examiner

Primary Examiner—Elizabeth F. McElwain
Assistant Examiner—Stuart Baum
(74) Attorney, Agent, or Firm—Knobbe Martens Olson & Bear LLP

(57) ABSTRACT

The present invention provides methods for using enhanced expression of nucleotide sequences encoding a flavin-containing monooxygenase (FMO) and suitable homologs thereof, to elicit desired traits, study biochemical pathways, and oxidize xenobiotics in plants.

35 Claims, 3 Drawing Sheets

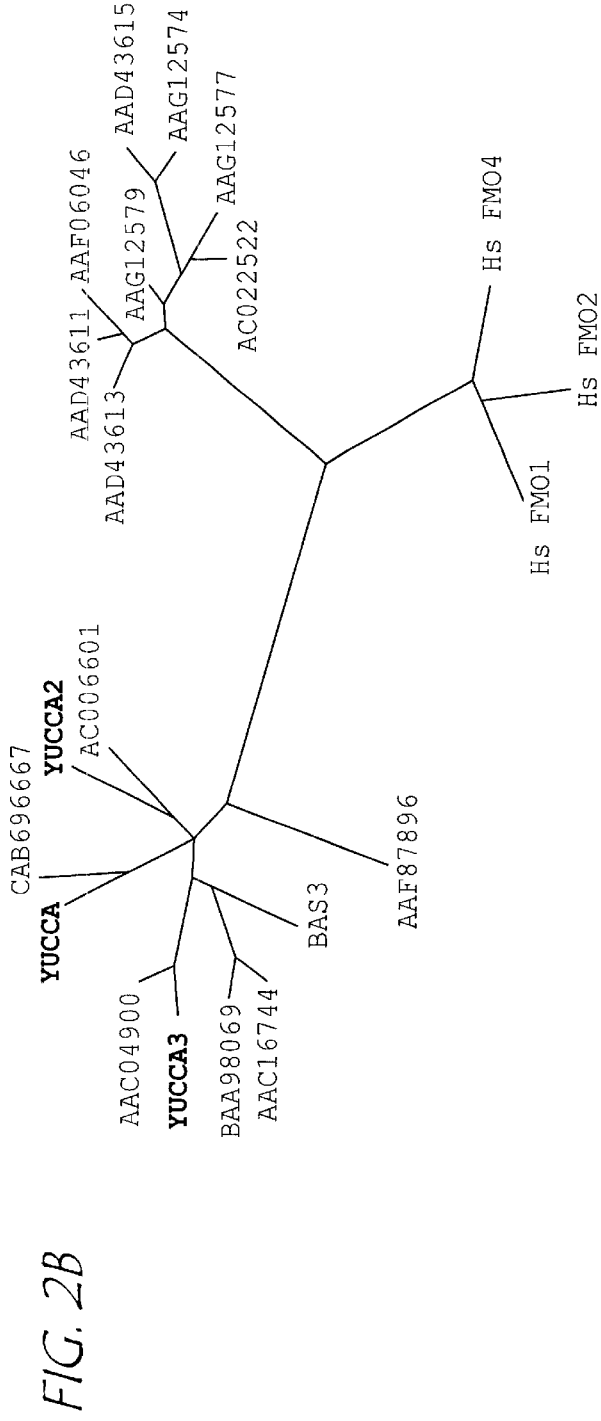

FIG. 2A

MESHPHNKTDQTQHIILVHGPIIIGAGPSGLATSACLSSRGVPSLIIERSDSIASLWKSKT
YDRLRLHLPKHFCRLPLLDFPEYYPKYPSKNEFLAYLESYASHFRIAPRFNKNVQNAAYDS
SSGFWRVKTHDNTEYLSKWLIVATGENADPYFPEIPGRKKFSGGKIVHASEYKSGEEFRRQ
KVLVVGCCGNSGMEISLDLVRHNASPHLVVRNTVHVLPREILGVSTFGVGMTLLKCLPLRLV
DKFLLMANLSFGNTDRLGLRRPKTGPLELKNVTGKSPVLDVGAMSLIRSGMIQIMEGVKE
ITKKGAKFMDGQEKDFDSIIFATGYKSNVPTWLQGGDFFTDDGMPKTPFPNGWRGGKGLYT
VGFTRRGLLGTASDAVKIAGEIGDQWRDEIKGSTRNMCSSRFVETSKS

FIG. 2B

SEQUENCE LISTING

<160> NUMBER OF SEQ ID NOS: 6

<210> SEQ ID NO 1

-continued

```
<211> LENGTH: 1245
<212> TYPE: DNA
<213> ORGANISM: Arabidopsis Thaliana
<220> FEATURE:
<221> NAME/KEY: CDS
<222> LOCATION: (1)...(1245)

<400> SEQUENCE: 1 atg gag tct cat cct cac aac aaa act gac cag acc cag cat atc atc     48
Met Glu Ser His Pro His Asn Lys Thr Asp Gln Thr Gln His Ile Ile
 1               5                  10                  15 ctc gta cat ggt ccc atc atc atc gga gct ggc cct tct ggt ctt gcc     96
Leu Val His Gly Pro Ile Ile Ile Gly Ala Gly Pro Ser Gly Leu Ala
             20                  25                  30 act tca gca tgt ctc tcg agc cgt gga gtc cct tct ttg atc cta gaa    144
Thr Ser Ala Cys Leu Ser Ser Arg Gly Val Pro Ser Leu Ile Leu Glu
         35                  40                  45 cgg tcg gat tca ata gca tct cta tgg aaa tct aaa acc tac gac cga    192
Arg Ser Asp Ser Ile Ala Ser Leu Trp Lys Ser Lys Thr Tyr Asp Arg
     50                  55                  60 ctc aga ctc cat ctc cca aaa cac ttt tgc cgg tta ccc ctc ctg gac    240
Leu Arg Leu His Leu Pro Lys His Phe Cys Arg Leu Pro Leu Leu Asp
 65                  70                  75                  80 ttc cct gaa tat tac cca aaa tac cct tcc aaa aac gag ttc ttg gcc    288
Phe Pro Glu Tyr Tyr Pro Lys Tyr Pro Ser Lys Asn Glu Phe Leu Ala
                 85                  90                  95 tac ctt gag tcc tac gct tcc cac ttc cgc atc gct cca agg ttc aac    336
Tyr Leu Glu Ser Tyr Ala Ser His Phe Arg Ile Ala Pro Arg Phe Asn
            100                 105                 110 aag aac gta caa aac gca gct tac gat tct tcc tcc ggt ttc tgg aga    384
Lys Asn Val Gln Asn Ala Ala Tyr Asp Ser Ser Ser Gly Phe Trp Arg
        115                 120                 125 gta aag act cat gat aac aca gag tac ctc tcc aaa tgg ctt atc gta    432
Val Lys Thr His Asp Asn Thr Glu Tyr Leu Ser Lys Trp Leu Ile Val
    130                 135                 140 gcc acc ggt gag aac gca gat cca tac ttc ccc gag att cca ggg aga    480
Ala Thr Gly Glu Asn Ala Asp Pro Tyr Phe Pro Glu Ile Pro Gly Arg
145                 150                 155                 160 aag aag ttt tcc ggc gga aaa atc gtt cac gcg agt gag tac aaa agc    528
Lys Lys Phe Ser Gly Gly Lys Ile Val His Ala Ser Glu Tyr Lys Ser
                165                 170                 175 ggc gaa gag ttc cgg cgg cag aaa gtt ttg gtt gtc gga tgt gga aat    576
Gly Glu Glu Phe Arg Arg Gln Lys Val Leu Val Val Gly Cys Gly Asn
            180                 185                 190 tcc ggc atg gaa att agc tta gac ctc gtc cga cat aac gca tct cct    624
Ser Gly Met Glu Ile Ser Leu Asp Leu Val Arg His Asn Ala Ser Pro
        195                 200                 205 cat ctt gtt gtc cgg aac acc gtt cat gtg ttg cca agg gag ata ctt    672
His Leu Val Val Arg Asn Thr Val His Val Leu Pro Arg Glu Ile Leu
    210                 215                 220 ggg gta tca aca ttt gga gtt gga atg aca ctt ctc aaa tgc tta ccc    720
Gly Val Ser Thr Phe Gly Val Gly Met Thr Leu Leu Lys Cys Leu Pro
225                 230                 235                 240 tta agg ctc gtt gac aag ttc ttg tta ttg atg gcc aat ctt tcg ttt    768
Leu Arg Leu Val Asp Lys Phe Leu Leu Leu Met Ala Asn Leu Ser Phe
                245                 250                 255 gga aat acc gac cgg ttg ggc ctt cgc cga cca aaa acg ggt ccg ctt    816
Gly Asn Thr Asp Arg Leu Gly Leu Arg Arg Pro Lys Thr Gly Pro Leu
            260                 265                 270 gag ctg aaa aac gtc acc ggc aaa agt ccg gtt ctc gat gtc gga gct    864
Glu Leu Lys Asn Val Thr Gly Lys Ser Pro Val Leu Asp Val Gly Ala
```

-continued

```
                    275                 280                 285
atg tct ctc atc aga tcc ggc atg att cag ata atg gaa ggt gta aag        912
Met Ser Leu Ile Arg Ser Gly Met Ile Gln Ile Met Glu Gly Val Lys
    290                 295                 300 gaa ata aca aag aaa gga gca aag ttt atg gat ggt caa gaa aag gac        960
Glu Ile Thr Lys Lys Gly Ala Lys Phe Met Asp Gly Gln Glu Lys Asp
305                 310                 315                 320 ttt gac tct atc ata ttt gcc act ggt tac aaa agc aac gtg cct act       1008
Phe Asp Ser Ile Ile Phe Ala Thr Gly Tyr Lys Ser Asn Val Pro Thr
                325                 330                 335 tgg ctt cag gga ggt gat ttt ttc acg gac gat ggg atg ccg aaa acg       1056
Trp Leu Gln Gly Gly Asp Phe Phe Thr Asp Asp Gly Met Pro Lys Thr
                340                 345                 350 ccg ttt cct aac ggc tgg aga gga ggg aaa gga ttg tac aca gtt ggt       1104
Pro Phe Pro Asn Gly Trp Arg Gly Gly Lys Gly Leu Tyr Thr Val Gly
            355                 360                 365 ttt acg aga aga gga ctc ctt gga acg gcg tct gac gcc gtt aag atc       1152
Phe Thr Arg Arg Gly Leu Leu Gly Thr Ala Ser Asp Ala Val Lys Ile
370                 375                 380 gct ggc gaa att ggt gac cag tgg aga gac gaa atc aag ggg tcc acc       1200
Ala Gly Glu Ile Gly Asp Gln Trp Arg Asp Glu Ile Lys Gly Ser Thr
385                 390                 395                 400 agg aat atg tgc agt tct cgt ttt gtc ttt acc tct aaa tcc taa           1245
Arg Asn Met Cys Ser Ser Arg Phe Val Phe Thr Ser Lys Ser  *
                405                 410
```

<210> SEQ ID NO 2
<211> LENGTH: 414
<212> TYPE: PRT
<213> ORGANISM: Arabidopsis Thaliana

<400> SEQUENCE: 2

```
Met Glu Ser His Pro His Asn Lys Thr Asp Gln Thr Gln His Ile Ile
 1               5                  10                  15

Leu Val His Gly Pro Ile Ile Gly Ala Gly Pro Ser Gly Leu Ala
             20                  25                  30

Thr Ser Ala Cys Leu Ser Ser Arg Gly Val Pro Ser Leu Ile Leu Asx
         35                  40                  45

Arg Ser Asp Ser Ile Ala Ser Leu Trp Lys Ser Lys Thr Tyr Asp Arg
     50                  55                  60

Leu Arg Leu His Leu Pro Lys His Phe Cys Arg Leu Pro Leu Leu Asp
 65                  70                  75                  80

Phe Pro Glu Tyr Tyr Pro Lys Tyr Pro Ser Lys Asn Glu Phe Leu Ala
                 85                  90                  95

Tyr Leu Glu Ser Tyr Ala Ser His Phe Arg Ile Ala Pro Arg Phe Asn
            100                 105                 110

Lys Asn Val Gln Asn Ala Ala Tyr Asp Ser Ser Gly Phe Trp Arg
        115                 120                 125

Val Lys Thr His Asp Asn Thr Glu Tyr Leu Ser Lys Trp Leu Ile Val
    130                 135                 140

Ala Thr Gly Glu Asn Ala Asp Pro Tyr Phe Pro Glu Ile Pro Gly Arg
145                 150                 155                 160

Lys Lys Phe Ser Gly Gly Lys Ile Val His Ala Ser Glu Tyr Lys Ser
                165                 170                 175

Gly Glu Glu Phe Arg Arg Gln Lys Val Leu Val Val Gly Cys Gly Asn
            180                 185                 190

Ser Gly Met Glu Ile Ser Leu Asp Leu Val Arg His Asn Ala Ser Pro
```

```
                195                 200                 205
His Leu Val Val Arg Asn Thr Val His Val Leu Pro Arg Glu Ile Leu
            210                 215                 220
Gly Val Ser Thr Phe Gly Val Gly Met Thr Leu Leu Lys Cys Leu Pro
225                 230                 235                 240
Leu Arg Leu Val Asp Lys Phe Leu Leu Leu Met Ala Asn Leu Ser Phe
                245                 250                 255
Gly Asn Thr Asp Arg Leu Gly Leu Arg Arg Pro Lys Thr Gly Pro Leu
            260                 265                 270
Glu Leu Lys Asn Val Thr Gly Lys Ser Pro Val Leu Asp Val Gly Ala
        275                 280                 285
Asn Ser Leu Ile Arg Ser Gly Met Ile Gln Ile Met Glu Gly Val Lys
        290                 295                 300
Glu Ile Thr Lys Lys Gly Ala Lys Phe Met Asp Gly Gln Glu Lys Asp
305                 310                 315                 320
Phe Asp Ser Ile Ile Phe Ala Thr Gly Tyr Lys Ser Asn Val Pro Thr
                325                 330                 335
Trp Leu Gln Gly Gly Asp Phe Thr Asp Asp Gly Met Pro Lys Thr
            340                 345                 350
Pro Phe Pro Asn Gly Trp Arg Gly Gly Lys Gly Leu Tyr Thr Val Gly
            355                 360                 365
Phe Thr Arg Arg Gly Leu Leu Gly Thr Ala Ser Asp Ala Val Lys Ile
        370                 375                 380
Ala Gly Glu Ile Gly Asp Gln Trp Arg Asp Glu Ile Lys Gly Ser Thr
385                 390                 395                 400
Arg Asn Met Cys Ser Ser Arg Phe Val Phe Thr Ser Lys Ser
                405                 410
```

```
<210> SEQ ID NO 3
<211> LENGTH: 20
<212> TYPE: DNA
<213> ORGANISM: Artificial Sequence
<220> FEATURE:
<223> OTHER INFORMATION: Artificial Primer

<400> SEQUENCE: 3
ttgacagtga cgacaaatcg                                            20

<210> SEQ ID NO 4
<211> LENGTH: 18
<212> TYPE: DNA
<213> ORGANISM: Artificial Sequence
<220> FEATURE:
<223> OTHER INFORMATION: Artificial Primer

<400> SEQUENCE: 4
cgcgcattcc gttcttgc                                              18

<210> SEQ ID NO 5
<211> LENGTH: 28
<212> TYPE: DNA
<213> ORGANISM: Artificial Sequence
<220> FEATURE:
<223> OTHER INFORMATION: Artificial Primer

<400> SEQUENCE: 5
cgggatccga atggagtctc atcctcac                                   28

<210> SEQ ID NO 6
```

```
-continued

<211> LENGTH: 31
<212> TYPE: DNA
<213> ORGANISM: Artificial Sequence
<220> FEATURE:
<223> OTHER INFORMATION: Artificial Primer

<400> SEQUENCE: 6
cgggatccca cgcaaattag gatttagagg t                              31
```

EXPRESSION OF FLAVIN-CONTAINING MONOXYGENASES IN PLANTS

Government Rights

This invention was made with government support under National Institutes of Health (NIH) grant # GM-52413, National Science Foundation (NSF) grant # MCB96-31390, and NSF grant # MCB97-23823. The government may have certain rights in the invention.

FIELD OF THE INVENTION

This invention relates generally to the field of genetic engineering in plants. This invention relates more specifically to methods of enhancing traits in plants, methods of determining plant growth regulator signal transduction pathways, and methods of utilizing plant flavin-containing monooxygenases.

BACKGROUND OF THE INVENTION

Auxin Biosynthesis and Effects

Auxin is an essential plant hormone that influences many aspects of plant growth and development including cell division and elongation, differentiation, tropisms, apical dominance, senescence, abscission and flowering. (Hooley, Plant Cell (1998) 10:1581–4). Not only is auxin a plant growth regulator, it is also likely to be a morphogen. (Sabatini et al., Cell (1999) 99:463–472). Although auxin has been studied for more than 100 years, its biosynthesis, transport, and signaling pathways remain elusive. In order to understand the biological functions of auxin, it is necessary to elucidate how auxin is synthesized, transported, and used as a signaling agent.

Indole-3-acetic acid (IAA), the first auxin to be chemically identified, appears to be the major endogenous auxin. (Davies, The Plant Hormones: Their Nature, Occurrence, and Functions (1995) Kluwer Academic Publishers, 1–12). Based on its structural similarities, tryptophan has been proposed as the auxin biosynthesis precursor. (Bartel, Ann Rev Plant Physiol (1997) 48:51–66). Many pathways have been proposed for converting tryptophan to IAA, but at present, none has been definitely proven. Tryptophan can be converted to indole-pyruvate by transferring the amino group. Indole-pyruvate can be further converted to indole-acetaldehyde, which can be oxidized to IAA. Tryptamine, a decarboxylated product of tryptophan, has also been proposed as an auxin biosynthesis intermediate. It was proposed that tryptamine is converted to indole-acetaldehyde by amine oxidase.

In addition, a P450-type monooxygenase has recently been found to catalyze the conversion of tryptophan to indole-acetaldoxime that can then be converted to indole-acetonitrile. (Bartel, Ann Rev Plant Physiol (1997) 48:51–66). Acetonitrile can be used as nitrilase substrate to generate auxin. In bacteria, tryptophan is converted to indole-acetamide by tryptophan monooxygenase. In addition, experiments with tryptophan auxotroph mutants have revealed a tryptophan-independent auxin biosynthesis pathway. In light of the fact that there are many possible auxin synthesis pathways, it is not surprising that no auxin deficient mutants have been isolated in the many genetic screens that have been carried out using a variety of plant species.

Another approach in finding auxin mutants has been to isolate gain-of-function mutants, for example, auxin over-production mutants. Several Arabidopsis mutants having elevated free auxin levels have been isolated from EMS mutagenesis screens. To date, all reported auxin overproducing mutants are recessive mutations. Mutations at the superroot locus (sur1) (Boejan et al., Plant Cell (1995) 7:1405), which is allelic to rooty (King et al., Plant Cell (1995) 7: 2023), hookless3 (Lehman et al., Cell (1996) 85:183), and alf1 (Luschnig et al., Genes Dev (1998) 12:2175), produce a phenotype having lateral root proliferation, epinastic leaves, and long hypocotyls. Sur2 mutants (Delarue et al., Plant J (1998) 14:603–611) have higher endogenous free auxin levels, but mutations at the sur2 locus are neither genetically nor phenotypically stable. In homozygous sur2 populations, a few plants having the wild-type (nonmutant) phenotype are observed in each generation. Homozygous sur1 usually does not produce true leaves and never sets any seeds. Thus, although cloning of sur1 and sur2 will help in understanding the auxin biosynthetic pathway, the infertile SUR mutant loci are not the most desirable for identification of other cellular components involved in auxin biosynthesis. Instead, a fertile auxin overproducing mutant would be more useful than the sterile auxin overproducing mutants that have so far been isolated.

Auxin is believed to be synthesized in the shoot and, for example, transported to the root tip to initiate root growth and elongation. Polar auxin transport is mediated by auxin efflux carriers and influx carriers. PIN (Steinmann et al., Science (1999) 286:316; Galweiler et al., Science (1998) 282:2226) and EIR1/PIN2/AGR1 (Marchant et al., Embo J (1999) 18:2066; Muller et al., Embo J (1998) 17:6903), which are homologous to bacterial membrane transporters, are considered to be putative efflux carriers in the shoot and root respectively. On the other hand, AUXI (Marchant et al., Embo J (1999) 18:2066), an amino acid permease homolog, is considered a possible auxin influx carrier. Other components including TIR3 have also been found to be important for auxin polar transport. Since auxin polar transport is important for plant tropisms and plant development, understanding this process is useful for determining the molecular basis in regulating plant pattern and development. A dominant auxin overproducing mutant would be very useful in defining how auxin transport is involved in regulation of plant organ development.

Some of the mechanisms involved in auxin signaling are better understood than the pathways of auxin biosynthesis and transport. The auxin signaling components that are presently known have been identified either by biochemical methods or by genetic screens for altered response to exogenously added auxin. In one method, following auxin treatment, the AUX/IAA genes were found to be rapidly and specifically induced and to express short-lived transcriptional repressors (Abel and Theologis, Plant Physiol (1996) 111:9); however, the expression pathway is not fully understood. AUX/IAA genes were also found to associate with other DNA binding proteins such as auxin response factors (ARFs) to modulate gene expression. (Hooley, Plant Cell (1998) 10:1581). Another class of auxin response mutants showed a diminished response to exogenous auxin, including the axr1 or TIR1 mutants, which are thought to regulate protein turnover in an auxin dependent manner. (Leyser et al. Nature (1993) 364:161; Ruegger et al., Genes Dev (1998) 12:198) The axr1 gene product AXR1 is a component of the ubiquitin-mediated protein degradation pathway.

All the components of the auxin signaling pathways that have been identified so far are components that act downstream from the auxin sensing step. Therefore, gaps in knowledge remain in the current understanding of the auxin signaling pathway that begins with auxin sensing, through activation of transcription factors, to downstream effectors.

A dominant auxin-overproducing mutant would provide an ideal tool for identifying components of the auxin signaling pathway.

Flavin-Containing Monooxygenases

Flavin-containing monooxygenases (FMOs) have a unique ability to oxidize structurally dissimilar compounds. Compared to the P450 family of monooxygenases, there are relatively few FMOs. Some FMOs have a plurality of isozymes, but the precise characterization of and specific function of each isozyme is not well understood.

The FMO group of enzymes is known to be important in the metabolism of a variety of drugs and toxins. The relative abundance of FMOs in most mammalian tissues and their loose substrate specificity suggests that they contribute substantially to detoxification of xenobiotics. The FMOs of rat, pig and rabbit are microsomal xenobiotic-metabolizing enzymes which oxidize various xenobiotics including drugs, agricultural chemicals, and environmental pollutants. It has recently been shown that population-specific polymorphisms of the human FMO3 gene have significance for detoxification of chemicals to protect humans from the potentially toxic properties of drugs and chemicals. (Cashman, *Drug Metab Dispos* (2000) 28:169).

SUMMARY OF THE INVENTION

The present invention provides methods for using enhanced expression of nucleotide sequences encoding flavin-containing monooxygenases, hereinafter "FMOs", to elicit desired traits, determine biochemical pathways, and oxidize xenobiotics. In one embodiment, the flavin-containing monooxygenase is from *Arabidopsis thaliana* and the FMO is an *Arabidopsis thaliana*-FMO (AT-FMO).

Embodiments of the present invention provide a method of enhancing at least one trait in a plant comprising transforming a plant with an expression vector encoding at least one FMO, expressing the FMO(s) encoded by the vector, and measuring the trait(s). The enhanced traits include, but are not limited to, enhanced expression of a FMO, increased hypocotyl elongation, increased root thickness, increased root hair development, increased lateral root initiation, increased apical dominance, epinastic leaf growth, increased flowering node formation, increased fruit yield, increased endogenous auxin levels, parthenocarpic fruit production, altered gene expression, altered pathogen resistance, altered pest resistance, and altered herbicide resistance. In addition, the trait may convey altered sensitivity to a plant growth regulator selected from the group consisting of auxins and chemicals having auxin-like activity, gibberellins, cytokinins, abscisic acid, ethylene, brassinosteroids, salicylates, and jasmonates.

Embodiments of the present invention provide a plant transformed with an expression vector encoding at least one FMO, wherein one or more sequences encoding FMO(s) are operably linked with one or more promoters or other regulatory sequences. Embodiments of the present invention further provide a plant transformed with an expression vector encoding at least one FMO, wherein expression of the FMO(s) may be regulated by a constitutive promoter, an inducible promoter, a tissue-specific promoter, or other promoters suitable for use in the invention.

Embodiments of the present invention further provide a method for identifying steps of auxin biosynthesis by transforming a plant with an expression vector encoding at least one FMO, expressing the FMO(s) encoded by the vector, carrying out a suppression screening of transformed plant material expressing the FMO(s), and measuring auxin biosynthesis. In other embodiments of the invention, suppression screening to identify steps of auxin biosynthesis include, but are not limited to, use of screening techniques wherein loss-of-function mutations are exposed, and screening techniques wherein gain-of-function mutations are exposed.

Another embodiment of the present invention provides a method for identifying steps of signal transduction pathways by transforming a plant with an expression vector encoding at least one FMO, expressing the FMO(s), carrying out suppression screening of transformed plants expressing the FMO(s), and measuring altered signal transduction. In other embodiments of the invention, suppression screening to identify steps of signal transduction pathways include, but are not limited to, use of screening techniques wherein loss-of-function mutations are exposed, and screening techniques wherein gain-of-function mutations are exposed.

Another embodiment of the present invention further provides a method for identifying a plant growth regulator by exposing a substrate molecule to at least one FMO to generate a modified substrate molecule, and measuring plant responses to the modified substrate molecule. In one embodiment, more than one modified substrate molecule is produced, and responses to more than one substrate molecule are measured. In another embodiment, responses to one or more modified substrate molecule are measured using a gene array. In yet another embodiment, responses to one or more modified substrate molecule are measured by measuring traits including, but not limited to, auxin levels, hypocotyl length, hypocotyl cell length, cotyledon thickness, cotyledon length, lateral root initiation, root hair number, leaf thickness, leaf epinasty, leaf angle, number of flowering nodes, flowering phenology, fruit development, parthenocarpy, protein content, amino acid profile, gene transcription, and gene expression.

Yet another embodiment of the invention further provides a method for studying the interaction between at least two growth regulators by transforming a plant with an expression vector encoding at least one FMO, expressing the FMO(s), and measuring responses to growth regulators. In one embodiment, at least one plant growth regulator is externally applied.

Still another embodiment of the invention is a method for studying root development comprising transforming a plant with an expression vector encoding at least one FMO, expressing the FMO(s), and measuring indicia of root development including, but not limited to, length, diameter, morphology, rate of elongation, root hair development, lateral root initiation, anthocyanin content, and root orientation. One embodiment provides a method for studying root development in which the plant transformed with, and expressing, at least one FMO is treated with an auxin transport inhibitor and development of club root morphology is measured.

Another embodiment of the invention provides a method for enhancing tryptamine degradation in plants transformed with and expressing at least one FMO.

One embodiment of the present invention provides a method for identifying at least one xenobiotic compound in a sample, where the xenobiotic is exposed to at least one FMO and the oxidized xenobiotic is measured by means that include, but are not limited to, chromatographic analysis, mass spectrometry, or biological assays. This method for identifying at least one xenobiotic can be used as a drug screening assay.

The FMO(s) can be used to detoxify a xenobiotic. In addition, a method is provided for producing an enzyme having xenobiotic detoxifying activity by transforming a host cell with an expression vector encoding at least one FMO and recovering fractions containing FMO activity.

Embodiments of the present invention further provide a light-sensitive promoter useful for placing downstream nucleotide sequences under regulation by specific wavelengths of light.

Another embodiment of the present invention provides a method of identifying inhibitors of FMO(s) by exposing FMO(s), or plants expressing FMO(s) to potential inhibitors and measuring FMO activity.

The above and other embodiments, features, and advantages of the present invention will be better understood from the following detailed descriptions taken in conjunction with the accompanying drawings, which is given by way of illustration only and is not limitative of the present invention.

BRIEF DESCRIPTION OF THE DRAWINGS

FIG. 2. YUCCA encodes flavin-containing monooxygenases. A) Amino acid sequence of FMO (SEQ ID NO: 2). Putative FAD binding motif near the amino-terminus and the putative NADPH binding motif near the middle of the protein are indicated in bold. B) Phylogenetic tree of the gene products of YUCCA and its homologs, related Arabidopsis genes, and human FMOs. GenBank accession numbers are shown.

DETAILED DESCRIPTION

Figure 1:
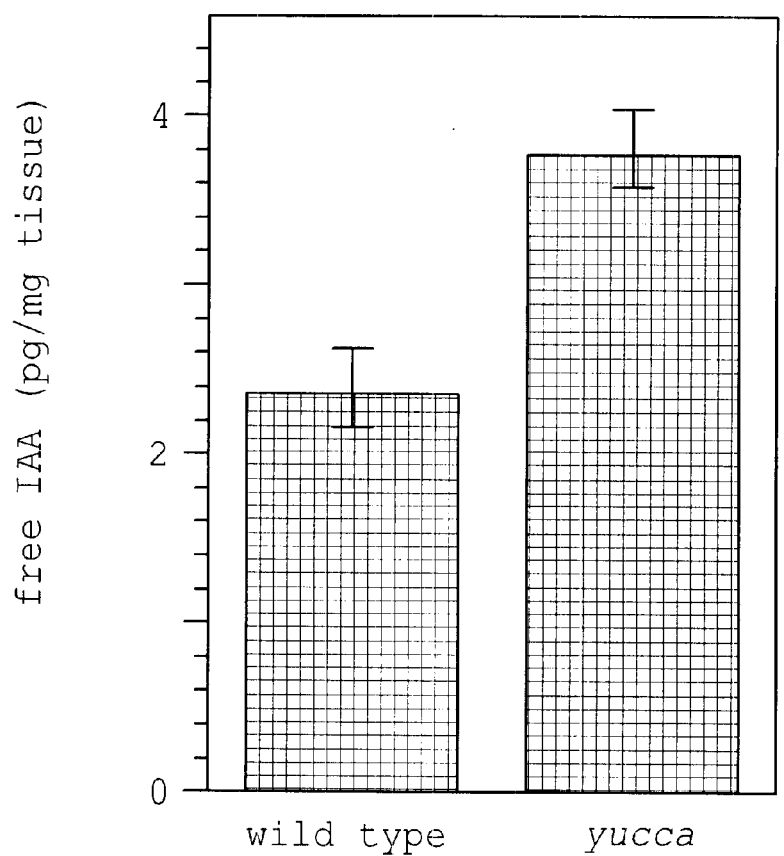
FIG. 1. Evidence for elevated levels of endogenous auxin in yucca, as demonstrated by GC-MS analysis of free IAA levels in wild type (WT) and yucca.
Figure 3:
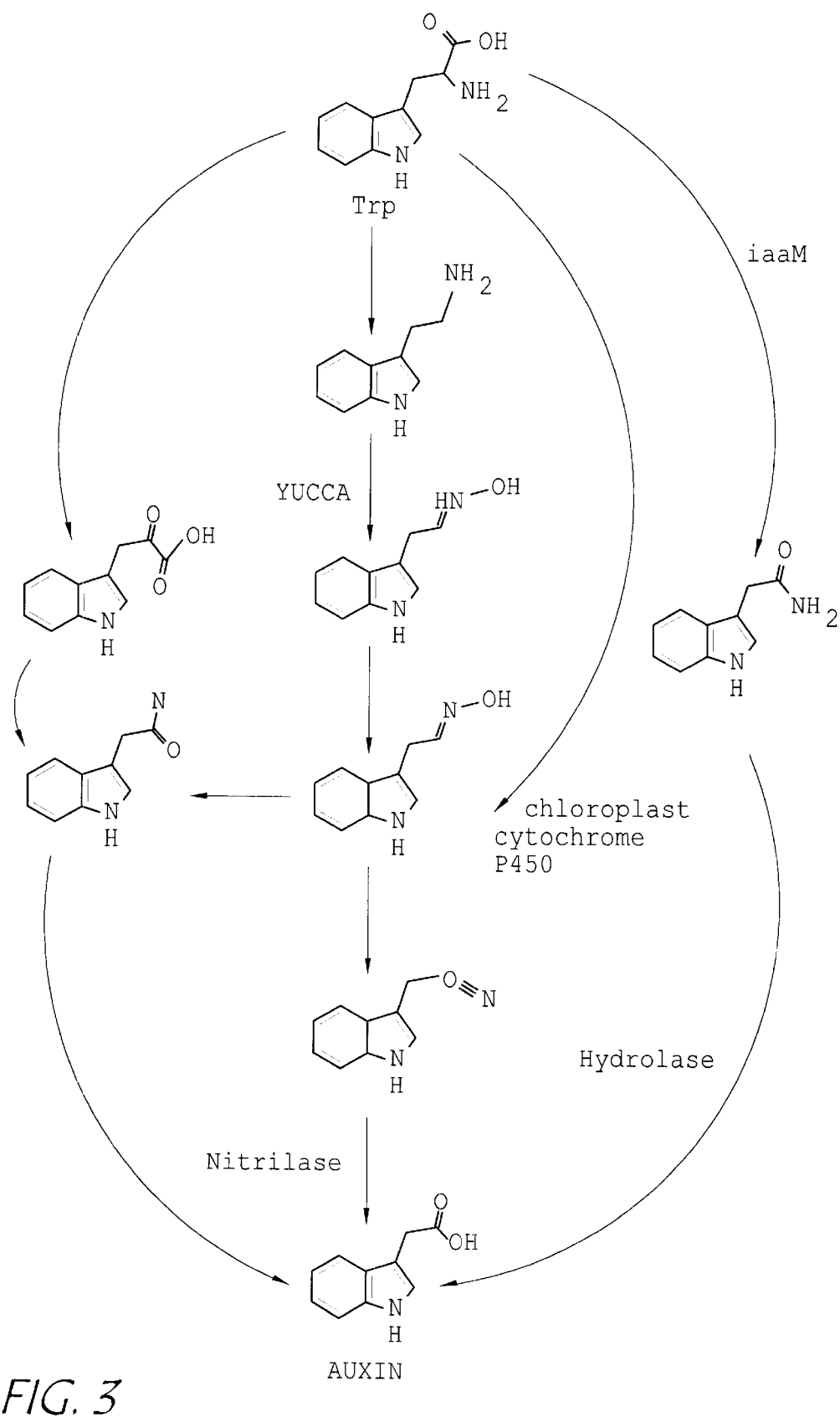
FIG. 3. YUCCA catalyzes a key step in auxin biosynthesis. Proposed putative tryptophan-dependent auxin biosynthesis pathways and intermediates are shown in diagram.

Definitions and terminology. By convention, a wild-type gene sequence is represented in upper case italic letters. For purposes of describing embodiments of the present invention, YUCCA denotes the FMO gene from *Arabidopsis thaliana* (SEQ ID NO: 1) whose enhanced expression leads to the yucca mutant phenotype. The term "yucca mutant phenotype" as used herein, refers to the phenotype produced by enhanced expression of the YUCCA gene, or the phenotype produced by any YUCCA homolog having the same effect when expressed in a host cell. The yucca mutant phenotype is characterized by, but is not limited to, long hypocotyls and internodes, increased root thickness, increased root hair development, increased lateral root initiation, increased endogenous auxin levels, and increased apical dominance.

The product of the YUCCA gene (SEQ ID NO. 1) is the YUCCA protein with the amino acid sequence of SEQ ID NO. 2, which has homology to flavin-containing monooxygenases (FMOs) and exhibits FMO enzymatic activity against suitable substrates. The YUCCA polypeptide having SEQ ID NO. 2 and all homologs thereof having the same biological activity when expressed in a host cell are herein referred to as FMOs, wherein FMO further refers to a gene product that is characterized, in part, by having an amino acid sequence that has at least about 35% identity with the amino acid sequence of SEQ ID NO. 2. Other embodiments include amino acid sequences that have at least 40%, 45%, 50%, 55%, 60%, 65%, 70%, 75%, 80%, 85%, 90%, and 95% identity with the amino acid sequence of SEQ ID NO. 2.

Enhanced expression in plants of FMOs is believed to produce the yucca mutant phenotype as described below. FMOs described herein include FMOs and homologs thereof isolated from *Arabidopsis thaliana*, rice or other plant species, wherein enhanced expression of these sequences produces the yucca mutant phenotype as described below. Identification of additional FMOs that produce the yucca phenotype can be made through cloning techniques known to one of skill in the art, as described more fully in Sambrook et al. (*Molecular Cloning: A Laboratory Manual* (1989) Cold Spring Harbor Laboratory Press) and Ausubel et al. (*Current Protocols in Molecular Biology* (1994–1998) John Wiley and Sons (with updates)).

Embodiments of the invention that include host cells or host organisms of the invention include, but are not limited to, plant cells as well as microorganisms such as yeast and bacteria. The expression vector of the invention includes, but is not limited to, plasmid and phage expression vectors suitable for expression in plants, yeast, or bacteria. As used herein, the term "expression vector encoding at least one FMO" refers to an expression vector comprising a nucleotide sequence encoding and FMO polypeptide. In one example the polypeptide is SEQ ID NO. 2 or homologs thereof having the same biological effect on host cells. Embodiments of the present invention provide methods of exposing a substrate molecule to FMOs, where the FMOs may be found in a extract of transformed plant material expressing the FMOs, or the FMOs may be further purified. An extract containing FMOs may be a cell-free extract, or may be substantially cell-free.

"Gene" refers to a nucleic acid fragment that expresses a specific protein, preferably including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that encodes a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence preferably consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg (*Biochemistry of Plants* (1989) 15:1–82). It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and preferably include polyadenylation recognition sequences and other sequences encoding regulatory signals capable of affecting mRNA processing or gene expression. The polyadenylation signal is usually characterized by affecting the addition of polyadenylic acid tracts to the 3' end of the MRNA precursor. The use of different 3' non-coding sequences is exemplified by Ingelbrecht et al. (*Plant Cell* (1989) 1:671).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein refers to the transcription and stable accumulation of sense (mRNA) or anti sense RNA derived from the nucleic acid fragment of the invention. Expression may also refer to translation of mRNA into a polypeptide. "Overexpression" refers to the production of a gene product in transgenic organisms that exceeds levels of production in normal or non-transformed organisms.

"Altered levels" refers to the production of gene product (s) in transgenic organisms in amounts or proportions that differ from that of normal or non-transformed organisms.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al., *Meth Enzymol* (1987) 143:277) and particle-accelerated or "gene gun" transformation technology (Klein et al., *Nature* (1987) 327:70–73; U.S. Pat. No. 4,945,050).

Standard recombinant DNA and molecular cloning techniques used herein are well known in the art and are described more fully in Sambrook et al. (*Molecular Cloning: A Laboratory Manual* (1989) Cold Spring Harbor Laboratory Press: Cold Spring Harbor).

"Xenobiotic" means a drug, environmental toxin, agricultural chemical., or other chemical that is not produced by an organism and which may or may not have a harmful effect on an organism exposed to said xenobiotic.

As used herein, the term "plant" refers to a whole plant, a plant part, a plant cell, or a group of plant cells, such as plant tissue. Plantlets are also included within the meaning of "plant". Plants included in embodiments of the invention are any plants amenable to transformation techniques, including angiosperms, gymnosperms, monocotyledons and dicotyledons.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, rapeseed, field beans, soybeans, peppers, lettuce, peas, alfalfa, clover, cole crops or Brassica oleracea (e.g., cabbage, broccoli, cauliflower, brussel sprouts), radish, carrot, beats, eggplant, spinach, cucumber, squash, melons, cantaloupe, sunflowers and various ornamentals. Woody species include poplar, pine, sequoia, cedar, oak, etc.

Genetically modified plants are produced by contacting a plant cell with a nucleic acid construct as described above. In one embodiment the construct is contained within a vector. Vector(s) employed for transformation of a plant cell for shoot meristem expression comprise a nucleic acid sequence comprising at least one structural gene expressing a product of interest, operably associated with the promoter of the invention. The vector harboring the heterologous nucleic acid sequence can also contain one or more selectable marker genes so that the transformed cells can be selected from non-transformed cells in culture, as described herein.

As used herein, the term "marker" refers to a gene encoding a trait or a phenotype which permits the selection of, or the screening for, a plant or plant cell containing the marker. In one embodiment the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-beta-phosphotransferase, thymidine kinase, exanthineguanine phospho-ribosyltransferase and aminoglycoside 3'-O-phosphotransferase II. Other suitable markers will be known to those of skill in the art.

To commence a transformation process it is conventional to construct a suitable vector and properly introduce it into the plant cell. The details of the construction of the vectors then utilized herein are known to those skilled in the art of plant genetic engineering.

For example, the nucleic acid sequences can be introduced into plant cells using Ti plasmids, root-inducing (Ri) plasmids, and plant virus vectors. (For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9, and Horsch, et al., Science, 227:1229, 1985, both incorporated herein by reference).

One of skill in the art will be able to select an appropriate vector for introducing FMO nucleic acid sequences in a relatively intact state. Thus, any vector which will produce a plant carrying the introduced nucleic acid construct should be sufficient. Even a naked piece of nucleic acid would be expected to be able to confer the properties of this invention, though at low efficiency. The selection of the vector, or whether to use a vector, is typically guided by the method of transformation selected.

The transformation of plants in may be carried out in essentially any of the various ways known to those skilled in the art of plant molecular biology. (See, for example, Methods of Enzymology, Vol.153, 1987, Wu and Grossman, Eds., Academic Press, incorporated herein by reference). As used herein, the term "transformation" means alteration of the genotype of a host plant by the introduction of a nucleic acid construct as described herein.

For example, a construct can be introduced into a plant cell utilizing Agrobacterium tumefaciens containing the Ti plasmid. In using an A. tumefaciens culture as a transformation vehicle, it is advantageous to use a non-oncogenic strain of the Agrobacterium as the vector carrier so that normal non-oncogenic differentiation of the transformed tissues is possible. It is also preferred that the Agrobacterium harbor a binary Ti plasmid system. Such a binary system comprises 1) a first Ti plasmid having a virulence region essential for the introduction of transfer DNA (T-DNA) into plants, and 2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells (De Framond, Biotechnology, 1:262, 1983; Hoekema, et al., Nature, 303:179, 1983). Such a binary system is preferred because it does not require integration into Ti plasmid in Agrobacterium.

Methods involving the use of Agrobacterium include, but are not limited to: 1) co-cultivation of Agrobacterium with cultured isolated protoplasts; 2) transformation of plant cells or tissues with Agrobacteriun; or 3) transformation of seeds, apices or meristems with Agrobacterium.

In addition, gene transfer can be accomplished by in situ transformation by Agrobacterium, as described by Bechtold, et al., (C.R. Acad. Sci. Paris, 316:1194, 1993) and exemplified in the Examples herein. This approach is based on the vacuum infiltration of a suspension of Agrobacterium cells.

One method of introducing a nucleic acid construct of the invention into plant cells is to infect such plant cells, an explant, a meristem or a seed, with transformed Agrobacterium tumefaciens as described above. Under appropriate conditions known in the art, the transformed plant cells are grown to form shoots, roots, and develop further into plants.

Alternatively, a nucleic acid construct of the invention can be introduced into a plant cell by contacting the plant cell using mechanical or chemical means. For example, the nucleic acid can be mechanically transferred by microinjection directly into plant cells by use of micropipettes. Alternatively, the nucleic acid may be transferred into the plant cell by using polyethylene glycol which forms a precipitation complex with genetic material that is taken up by the cell.

A nucleic acid construct of the invention can also be introduced into plant cells by electroporation (Fromm, et al., Proc. Natl. Acad. Sci., U.S.A, 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing nucleic acid into a plant cell is high velocity ballistic penetration by small particles with the nucleic acid to be introduced contained either within the matrix of small beads or particles, or on the surface thereof (Klein, et al., Nature 327:70, 1987). Although, typically only a single introduction of a new nucleic acid sequence is required, this method particularly provides for multiple introductions.

Cauliflower mosaic virus (CaMV) may also be used as a vector for introducing a nucleic acid construct of the invention into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

Typically, the nucleic acid construct is introduced into a plant cell by contacting the cell with a vector containing the promoter-nucleic acid sequence encoding the protein of interest construct. As used herein, the term "contacting" refers to any means of introducing the vector(s) into the plant cell, including chemical and physical means as described above. In one embodiment, contacting refers to introducing the nucleic acid or vector into plant cells (including an explant, a meristem or a seed), via *Agrobacterium tumefaciens* transformed with the heterologous nucleic acid as described above.

Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension, to the stage of ripening and germination as natural embryos. The culture media will generally contain various amino acids and hormones, necessary for growth and regeneration. Examples of hormones utilized include auxin and cytokinins. It is sometimes advantageous to add glutamic acid and proline to the medium, especially for such species as corn and alfalfa. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration (see Methods in Enzymology, Vol. 118 and Klee, et al., Annual Review of Plant Physiology, 38:467, 1987). Utilizing the leaf disk-transformation-regeneration method of Horsch, et al., Science, 227:1229, 1985, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by the taking of cuttings or by tissue culture techniques to produce multiple identical plants. Selection of desirable transgenotes is made and new varieties are obtained and propagated vegetatively for commercial use.

In seed propagated crops, the mature transgenic plants can be self-crossed to produce a homozygous inbred plant. The inbred plant produces seed containing the newly introduced foreign gene(s). These seeds can be grown to produce plants that would produce the selected phenotype, e.g. early flowering.

Parts obtained from the regenerated plant, such as flowers, seeds, leaves, branches, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

Embodiments of the invention include a plant produced by the method of the invention, including plant tissue, seeds, and other plant cells derived from the genetically modified plant.

Embodiments of the present invention can be practiced by transforming a host cell or host organisms with an expression vector encoding at least one FMO and expressing the FMO(s) encoded by the expression vector. As one example the YUCCA gene isolated from *Arabidopsis thaliana* may be inserted into Arabidopsis and expressed, or may be transformed into other plant or non-plant hosts. One embodiment of the present invention provides enhanced expression of the YUCCA gene by including cauliflower mosaic virus (CaMV) 35S enhancer elements in the expression vector, as described in Weigel et al. (*Plant Physiol* (2000) 122:1003). In one embodiment, a BamHI/HpaI fragment containing the YUC coding region, 3 kb of upstream sequence, and 4 copies of 35S enhancer elements was cloned into the BanHI/SmaI site of a pPZP211 expression vector. In other preferred embodiments, other enhancer elements can be used, including the direct repeats C14 and A29 that have been used in maize and rice.

The level of YUCCA expression can also be regulated by linking a variety of promoters to the YUCCA gene. Expression experiments in Arabidopsis revealed that the YUCCA coding region is under the control of the endogenous promoter, which is light-regulated. Of course YUCCA can be regulated by using chimeric molecules created when the YUCCA coding region is operably linked with other promoters, including but not limited to, constitutive promoters, especially constitutive overexpressing promoters, inducible promoters, and tissue-specific promoters. Inducible promoters include promoters regulated by light, temperature, nutritional or developmental status of the plant, endogenous chemicals or exogenous chemicals. U.S. Pat. No. 6,063,985 to Chua et al. discloses a chemically inducible promoter that is induced by exogenous chemicals, namely glucocorticoids that do not naturally occur in plants.

Structure of YUCCA. The YUCCA gene was discovered by activation tagging in Arabidobsis (Weigel et al., *Plant Physiol* (2000) 122:1003) and observation of a resulting mutant phenotype which had narrower leaf blades and a semi-erect growth habit in the leaves of the adult plant. Northern blot results from mutant plants indicated that the presence of inserted CaMV 35S enhancers resulted in higher expression of a nucleotide sequence having the sequence of SEQ ID NO. 1, a dominant gene called YUCCA. This gene was found to have three introns and 4 exons. In addition, YUCCA encoded a polypeptide 414 amino acids long and having 25 percent overall sequence identity to a consensus FMO sequence, where the flavin-binding domain and NADPH-binding domain have greater homology to the consensus sequence. However, this invention is not limited to only the FMO discovered from Arabidobsis. Other FMOs and homologs of YUCCA that produce the yucca mutant phenotype when expressed in any plant are within the scope of this invention.

Database searches using BLAST (Altschul et al., *J. Mol. Biol.* (1990) 215:403) indicated the YUCCA family contains at least nine other proteins having amino acid identity of between 44–64% with YUCCA. These homologs correspond to protein sequences having GenBank Accession Numbers CAB41936, AAB80641, AAC04900, AAC16744, AAF87896, BAA98069, CAB96667, CAA22980 and a protein encoded by a locus on the nucleotide sequence having GenBank Accession Number AC006601.

As shown in FIG. 2b, there appear to be two families of FMO-like proteins encoded in the Arabidopsis genome. Other genes that encode FMOs may be located at other loci in the genome, and if overexpression of the gene has the same biological effect as YUCCA, then the other genes are functional paralogs of the YUCCA gene.

Enzymatic activity of the YUCCA gene product. In one experiment, the YUCCA gene was transformed into an *E. coli* overexpression vector and the recombinant YUCCA gene product, a polypeptide having the amino acid sequence of SEQ ID NO. 2, was recovered from the *E. coli* overexpression system. The YUCCA gene product (SEQ ID NO. 2) was enzymatically active and showed typical FMO activities, including NADPH oxidase activity. This polypeptide (SEQ ID NO. 2) was found to use tryptamine as a substrate to generate N-hydroxyl tryptamine. Thus, the amino acid sequence of SEQ ID NO: 2 can be used to metabolize tryptamine, whether endogenous or exogenous, as well as to generate N-hydroxyl tryptamine.

Phenotypes of the yucca mutant. The yucca mutant had distinct phenotypical features in all organs and at all stages of Arabidopsis development. At the seedling stage, yucca seedlings grown in white light had much longer hypocotyls (3.2 times longer) than the wild type (WT). Yucca had a hypocotyl length of 5.10±0.09 mm, and WT had a hypocotyl length of 1.52±0.04 mm. Yucca seedlings showed increased cell elongation, but not an increased rate of cell division, leading to the conclusion that the increased hypocotyl length in yucca was probably the result of greater cell elongation, not faster cell division. The yucca mutant cotyledons were dramatically different from those of WT, in that the yucca cotyledon petioles were much more elongated than WT, and the yucca cotyledons curled down. Compared to the wild-type, the yucca mutant had more root hairs, and the yucca root hairs were longer than that of WT. The primary root of the yucca mutant was thicker and shorter than the WT root.

The mature, adult yucca mutant also had a distinct phenotype. Mature yucca leaves had long petioles and the leaves are longer and narrower than WT leaves. In a mature plant, yucca leaves had a semi-erect growth habit, with epinastic curling leaves, giving rise to the mutant name because of the mature mutant Arabidopsis plant's resemblance to the yucca (Agave sp.) plant. The yucca mutant had increased apical dominance compared with WT. Flowers of the yucca mutant had short stamens and little pollen.

Enhanced expression of YUCCA in a plant also provided pleiotropic effects that enhanced traits including, but are not limited to, hypocotyl elongation, root thickness, root hair development, lateral root initiation, apical dominance, epinastic leaf growth, flowering node formation, fruit yield, endogenous auxin levels, parthenocarpic fruit production, gene expression, and pest resistance.

Light regulation of YUCCA expression. It was also discovered that expression of the yucca phenotype was differentially regulated by different wavelengths of light, demonstrating the presence of a novel light-regulated promoter that controls the YUCCA gene. In one embodiment, the yucca mutant was created in the WT background by transforming WT Arabidopsis with an expression vector comprising the YUCCA gene and at least one 35S enhancer (Weigel et al., *Plant Physiol* (2000) 122: 1003). In the WT background, the yucca mutant showed the following differences from the WT: yucca was slightly shorter (20%) than WT when grown in the dark; 3 times taller than WT when grown under white light; no different from WT when grown under red light; taller than WT when grown under far-red light and blue light.

In another experiment, the yucca mutant was created in the PHYA211 knockout background by transforming PHYA211 knockout Arabidopsis (the phya211 mutant) with an expression vector comprising the YUC gene and at least one 35S enhancer. The yucca/phya211 double mutant showed the following differences from the phya211 mutant: yucca was taller than phya211 when grown under white light; no different from phya211 when grown under red; and taller than phya211 when grown under blue light and far-red light.

Enhanced expression of the YUCCA gene overproduces auxin. Explants of yucca were found to proliferate in auxin-free media, while WT explants died under the same conditions. Massive root growth was observed when yucca explants grew in Murashige and Skoog (MS) media. Callus was induced by adding cytokinin, and young yucca plants that are regenerated in MS media containing cytokinin. A GUS reporter gene controlled by an auxin responsive element was expressed at much higher level in yucca. Direct GC-MS measurement of free IAA levels in yucca tissues revealed that yucca has 50% more endogenous free IAA. In addition, YUCCA appears to be involved in tryptophan-dependent auxin synthesis. Although tryptophan analogs such as 5-methyl tryptophan or 5-fluoro-tryptophan are normally toxic to plants because they inhibit tryptophan biosynthesis in plants and disrupt protein function when incorporated into proteins, yucca mutants were less sensitive to these tryptophan analogs. In the presence of 100 $\mu$M 5-methyl tryptophan, WT plant material died while yucca survived. In yucca, the 5-methyl tryptophan was converted to 5-methyl IAA.

In addition, the yucca mutant phenotype produced by enhanced expression of the YUCCA gene was seen in plants grown in white light or red light. By contrast, the iaam mutant phenotype is seen only when IAAM plants are grown in white light.

It was also discovered that auxin transport in yucca was blocked by application of transport inhibitor naphthylthalamic acid (NPA), resulting in yucca mutants having a giant root, called a "club root" due to its thick, short appearance. This club root was substantially thicker than the regular yucca root, which is already thicker than the WT root. The club root had a combination of rough and smooth surfaces, which may indicate the presence of two different cell types growing at different rates. The club root produced by blocking auxin transport in yucca mutants may provide an important tool for studying root growth and development. Yucca mutants treated with 50 $\mu$M NPA in the growth medium developed multiple club roots, while yucca mutants treated with 100 $\mu$M NPA in the growth medium developed a single club root. Wild type (WT) Arabidopsis did not develop a club root when auxin transport was blocked by treatment with NPA.

Enhanced expression of YUCCA affects plant growth regulator responses, signal transduction, and chemical interactions. As described herein, the yucca mutant had pleiotropic effects on plant growth regulator responses. Ethylene treatment was found to have little effect on the yucca mutant. However, treatment of yucca mutants with 5 $\mu$M 1-aminocyclopropane-1-carboxylate (ACC), an ethylene precursor, had differential effects on plant organs. ACC treatment suppressed the elongated yucca hypocotyl, but did not change the appearance of the yucca cotyledon. Treatment of yucca with 2 $\mu$M brassinazole (Brz), a brassinosteroid-biosynthesis-specific inhibitor, had a similar effect as that of ACC. Thus, enhanced YUCCA expression can be used to explore the signal transduction pathways and interactions of plant growth regulators including, but not limited to, auxins including IAA, chemicals having auxin-like activity, gibberellins, cytokinins, abscisic acid, ethylene, brassinosteroids, salicylates, and jasmonates. Other compounds having plant growth regulator activity may also be studied using the yucca mutant.

Using these methods, plant growth regulators can be identified by exposing a substrate molecule to at least one FMO to produce a modified substrate molecule, and then measuring whether the modified substrate molecule has plant growth regulator activity. For example, a recombinant polypeptide having the sequence of SEQ ID NO: 2 can produce N-hydroxyl-tryptamine when tryptamine is used as a substrate. Various means of measuring plant growth regulator activity can be used, including but not limited to measuring changes in gene expression. Gene expression can be measured by various means including the use of a gene array to measure expression levels of multiple genes. Effects on plant growth and development can be measured, and endogenous levels of modified substrate molecules having plant growth regulator activity can be measured.

A change in one plant growth regulator signal transduction pathway may affect another plant growth regulatory signal transduction pathway. Accordingly, another embodiment of the invention provides methods of determining interactions between plant growth regulator biosynthetic and signal transduction pathways by producing transformed plants having enhanced expression of FMOs and thereafter measuring responses to plant growth regulators in FMO-expressing plants.

In one embodiment, suppression screening exposes loss-of-function mutations in signal transduction pathways, and may be generated using ethylmethyl sulfonate (EMS). In another embodiment, suppression screening exposes gain-of-function mutations in signal transduction pathways, and may be generated by activation tagging. Embodiments of the present invention may be useful to identify steps in signal transduction pathways including, but not limited to, phototransduction, gravitropism, nutrient responses, plant growth regulator transduction, pathogenesis, wounding, and temperature sensing.

In one embodiment, tryptamine is used as the substrate, and N-hydroxyl-tryptamine is used as the modified substrate molecule. Thereafter, plant responses to the modified substrate molecule are measured using a gene array device such as those made by Affymetrix (Foster City, calif.).

In another embodiment, plant responses to the modified substrate molecule of an FMO are be determined by measuring plant traits consisting of: hypocotyl length, hypocotyl cell length, cotyledon thickness, cotyledon length, lateral root initiation, root hair number, leaf thickness, leaf epinasty, leaf angle, number of flowering nodes, flowering phenology, fruit development, protein content, amino acid profile, gene transcription, and gene expression.

Genetic Induction of Parthenocarpy. Auxin appears to play a role in parthenocarpy, the ability to set seedless fruits as discussed in PCT publication WO 97/30165 to Barg, et al. and PCT publication WO 98/28430 to Saedler. Accordingly, elevated levels of endogenous auxin found in the yucca mutants may provide a threshold concentration of auxin and other hormones, or otherwise alter plant metabolism in ways required for parthenocarpic fruit set. Thus, one method of inducing genetic parthenocarpy would be to transform plant cells with exogenous FMOs genes so that they overexpress the FMO resulting in increased auxin levels. Methods of inducing genetic parthenocarpy by transforming plants to express the rolB gene from the TL-DNA of Agrobacterium rhizogenes agropine-type Ri plasmid is disclosed in U.S. Pat. No. 6,114,602 to Barg, et al.

The YUCCA knock-out phenotype. A YUCCA knock-out mutant was identified by screening 10,000 T-DNA insertional Arabidopsis lines as described in Krysan et al. (*Proc Natl Acad Sci* (1996) 93:8145). Lines homozygous for the T-DNA insertion in the YUCCA gene did not show any dramatic changes in phenotype. In view of the fact that there are multiple YUCCA homologs in Arabidopsis, a single knock-out mutation in a single gene would not be expected to have a dramatic effect.

Enzymatic activity of FMOs. The enzymatic activity of any FMO may be assayed by a variety of means. In one embodiment of the invention, FMO enzymatic activity is measured by the method of Cashman (*Anal Biochem* (1987) 160:294), using direct analysis of quenched radiolabeled incubation substrates by thin-layer-chromatography. In another embodiment, FMO activity may be characterized by measuring the amount of modified substrate molecule produced, using various chromatographic techniques including but not limited to low pressure liquid chromatography, high performance liquid chromatography, affinity chromatography, ion-exchange chromatography, electrofocusing chromatography, molecular sieving chromatography and other chromatographic methods.

In another embodiment, mass spectrometry is used to measure and identify the modified substrate produced by the enzymatic activity of any FMO. Another embodiment of the present invention includes the use of biological and/or serological assays to measure the amount of modified substrate produced by FMO activity. Biological assays may include assays for stimulation or inhibition of various metabolic processes or target enzymes, and may include assays of the effects of a sample on a test organism. Biological assays may be used to determine the toxicity of a sample containing the modified substrate.

Oxidation of xenobiotics. One embodiment of the invention provides a drug screening assay, wherein measurement of the modified substrate is used to identify drug compounds present in a sample. This embodiment provides a means for quantifying the amount of the original drug present by measuring the amount of modified substrate present. This method is especially desirable when FMOs are incubated with a sample under conditions in which the FMO will oxidize all substrate present in a sample.

Detoxification of xenobiotics. The present invention includes embodiments wherein xenobiotics are detoxified by the oxidizing activity of at least one FMO. In one embodiment, a xenobiotic is exposed to at least one FMO and the reaction is allowed to proceed. After the reaction has taken place, toxicity measurements of the xenobiotic are made to determine whether the xenobiotic has or has not, and to what degree, been detoxified by the FMO. Other embodiments further provide a method of producing an enzyme having xenobiotic detoxifying activity by transforming a host cell with an expression vector encoding at least one FMO and recovering fractions having xenobiotic detoxifying activity.

The range of host cells and host organisms for this embodiment includes plant cells, bacterial cells, yeast cells, mammalian cells, and any other cell capable of being transformed with a suitable expression vector encoding at least one FMO. Fractions containing active enzyme having xenobiotic detoxifying activity may be recovered by lysing transformed host cells or by otherwise disrupting host cells; said fractions may be recovered as a cell-free extract, or may be substantially cell-free, as long as an acceptable level of xenobiotic detoxifying activity remains. When the expression vector used comprises signal sequences capable of directing the expressed AT-FMOs to be secreted, then the active enzyme fraction may be recovered from extracellular liquids or spaces, as well as from cell extracts. When the expression vector used comprises signal sequences capable of targeting the expressed AT-FMOs to an intracellular membrane or to the plasma membrane, then the active enzyme may be recovered from membrane fractions that may be pure, substantially pure, or mixed with cell contents.

Inhibitors of AT-FMOs. One embodiment of the invention provides a method of identifying FMO inhibitors by using FMOs. By way of example, Cashman et al. (*Biochem Pharmacol* (1999) 58:1047–1055) detected in vivo inhibition of functional human FMO activity in subjects eating a diet supplemented with indole-containing compounds, and subsequently identified in vitro inhibitors of FMOs from the pool of potential metabolites of the indole-containing compounds. One embodiment thus provides a method for exposing at least one FMO to a compound and testing the effect of the compound on FMO enzymatic activity. A decrease in FMO enzymatic activity demonstrates that a compound is an FMO inhibitor.

FMOs homologs in other species. Database searching showed that there are at least five FMO genes in the rice (*Oryza sativa*) database. Moreover, tobacco plants transformed to overexpress the Arabidopsis YUCCA gene showed a dramatic change in phenotype that included long narrow epinastic leaves very similar to the yucca leaf phenotype in Arabidopsis. These results indicate that the pathway(s) in which FMOs exert their functions are likely to be conserved among divergent plants.

The following examples are provided to illustrate embodiments of the present invention and should not be interpreted in any way to limit the scope of the invention. Those skilled in the art will recognize that various modifications can be made to the methods described herein while not departing from the spirit and scope of the present invention.

EXAMPLE 1

Identification of the YUCCA gene. As described in Weigel et al., (*Plant Physiol* (2000) 122: 1003) an activation tagging screen was carried out using *Arabidopsis thaliana*, with some screens carried out in wild type Arabidopsis and others carried out in well-characterized Arabidopsis mutants. The activation tagging plasmid pSK1074 that contains four copies of CaMV 35S enhancers was transformed into *Agrobacterium tumefaciens* strain GV 3101 (Weigel et al., *Plant Physiol* (2000) 122:1003) and the resulting bacterium was used to transform WT Arabidopsis Col-0 plants with the floral dipping method (Clough et al., *Plant J* (1998) 16:735). Seeds from the transformed plants were surface sterilized using previously described method and plated on 0.5× Murashige and Skoog media containing 1.5% sucrose, 0.8% phytoagar (Gibco Life Science Technology) and 30 μM kanamycin. Plates were wrapped with aluminum foil and incubated at 4° C. for 4 days to synchronize germination. Plates were incubated in white light for 4 hours to stimulate germination and then incubated at 23° C. in far-red light. After 6 days in far red light, candidates with longer hypocotyls was further incubated in white light for a few days until the hypocotyls greened. All the candidates were transferred to soil to set seeds.

In a screen of the phyA-211 Arabidopsis mutant that has a long hypocotyl, a mutant having a longer hypocotyl than phyA-211 in far-red light was identified as a phyA211 enhancer during an activation tagging screen for phyA211 suppressors and enhancers, and the mutant was named yuc-2D. An activation tagging screen carried out in the wild type germplasm also generated a yucca mutant, called yuc-1D. The genomic DNA adjacent to the right border of the T-DNA insertions in the two alleles was cloned by plasmid rescue.

EXAMPLE 2

Cloning of YUCCA. Plant DNA from about 100 mg fresh seedlings was prepared using the Phytopure plant DNA extraction kit (Nucleon Biosciences, Coatbridge, U.K.) kit. Plasmid rescue experiments were carried out as described inweigel et al. (*Plant Physiol* (2000) 122:1003). The CaMV 35S enhancer arrays in the two mutants had inserted within less than 3 kb of each other, downstream of the same coding region of the gene encoding GenBank Accession CAB79971. The plant DNA was digested with BamHI, EcoRI, and HindIII, respectively. The digested DNA was separated on a 1% agarose gel. The DNA was then transferred to a nylon membrane and probed with pBluescript SK. The southern blot detected a 10 Kb fragment from BamHI digestion, a 7 Kb fragment with EcoRi digestion, and a 5 kb fragment with HindIII digestion. EcoRI digestion was then used to rescue the plasmid. The EcoRI digested DNA was self-ligated with T4 DNA ligase. The ligation mixture was transformed into the XL-1-Blue strain of *E. coli* . Plasmids from individual colonies were digested with various restriction enzymes. Candidate plasmids were sequenced with the RB primer (5'-TTGACAGTGACGACAAATCG-3') (SEQ ID NO. 3) and EcoRI primer (5'-CGCGCATTCCGTTCTTGC-3') (SEQ ID NO. 4). The resulting partial sequences were used to search the Arabidopsis databases. The YUCCA coding region was identified through isolation and sequence identification of the cDNA.

The YUCCA cDNA was cloned using the following PCR primers: oligo1 (5'-CGGGATCCGAATGGAGTCTCATCCTCAC-3') (SEQ ID NO. 5) oligo 2 (5'-CGGGATCCCACGCAAATTAGGATTTAGAGGT-3') (SEQ ID NO. 6) with the cDNA from YUCCA as the template. The PCR fragment was gel-purified and cloned into a pGMT vector (Promega). The PCR fragment was sequenced to confirm that no mutations or error were introduced during PCR.

EXAMPLE 3

Northern blot and RT-PCR . A Northern blot was performed to detect RNA transcripts of YUCCA. Total RNA from 7-day old light grown seedlings was extracted with the TRIzol Reagent following the manufacturer's instructions. The protocol for Northern blot was described in references. (Sambrook et al. (*Molecular Cloning: A Laboratory Manual* (1989) Cold Spring Harbor Laboratory Press: Cold Spring Harbor) and Ausubel et al. (*Current Protocols in Molecular Biology* (1994–1998) John Wiley and Sons (with updates)) A PCR amplified genomic cDNA fragment was used as a probe.

RT-PCR was used to amplify part of the coding region of YUCCA. Total RNA from root, hypocotyl, and cotyledons of 5-day light grown seedlings was isolated as described above. cDNAs from 1 μg of total RNA were made using oligo dT (500 ng) and the reverse transcriptase. 5% of the cDNAs were used to set up PCR reactions. PCR conditions were: 94° C., 30 seconds; 64° C. 30 seconds; 72° C., 40 seconds, 25 cycles. Northern blot analysis of total RNA from both alleles that induced the yucca phenotype showed that the expression level of this gene was higher in yucca than in wild type. This indicated that the two mutants carried dominant alleles at the same locus.

EXAMPLE 4

Effects of overexpression of the YUCCA gene. The effects of overexpression of the YUCCA gene were determined by including cauliflower mosaic virus (CaMV) 35S enhancer elements in the expression vector, as described in Weigel et al. (*Plant Physiol* (2000) 122:1003). A BamHI/HpaI fragment containing the YUCCA coding region, 3 kb upstream sequence and 4 copies of 35S enhancer from the rescued plasmid were cloned into the pPZP211 expression vector at the BamHI/SmaI sites, and the resulting plasmid was transformed into wild-type *Arabidopsis thaliana* Col-0 to generate recapitulation lines. (Clough et al., *Plant J* (1998) 16: 735). Plants overexpressing YUCCA had the yucca mutant phenotype.

Phenotypic effects of YUCCA overexpression were determined by measuring hypocotyl elongation, root thickness, root hair development, lateral root initiation, apical dominance, leaf growth, flowering node formation, fruit yield, endogenous auxin levels, gene expression, and sensitivity to plant growth regulators.

EXAMPLE 5

Effect of YUCCA overexpression on endogenous auxin levels in Arabidopsis. To determine whether the YUCCA gene product has a role in the auxin biosynthetic pathway, YUCCA overexpressing Arabidopsis plants were generated using techniques described above to produce plants having the yucca mutant phenotype. Since the original yucca alleles were poorly fertile, recapitulaton lines with weaker phenotypes were used for further studies; these recapitulation lines are referred to as yucca mutants as well.

The amount of free IAA in tissues of yucca mutants was determined by direct gas chromatography-mass spectrometry measurements to determine endogenous IAA levels, as described in Chen et al. (*Plant Physiol* (1988) 86:822). Because the original yucca mutants were poorly fertile, it was necessary to use weak recapitulation lines to obtain a sufficient quantity of tissue to measure endogenous IAA levels. Tissues from recapitulation lines of yucca mutants had 50% more endogenous free IAA than wild-type tissues (FIG. 1). It is expected that a higher level of auxin is found in stronger lines of yucca mutants.

EXAMPLE 6

Increased IAA levels are physiologically significant. Physiological and genetic experiments were carried out to confirm that the increase in free IAA levels observed in yucca mutants is physiologically significant. It is known that Arabidopsis explants cannot proliferate with addition of auxin to the medium, and that the ration of auxin to cytokinin determines the relative growth of roots, shoots, and undifferentiated callus (Mathur et al., in *Arabidopsis Protocols,* Martinez-Zapater, Salinas, Eds. (1998) Vol 82: 31) When yucca and wild type cotyledon explants were grown in MS medium without auxin, the yucca explants proliferated with extensive root growth while the wild type explants did not proliferate at all. Addition of cytokinin to the medium reduced both the length and abundance of the yucca explant roots, whereas the wild-type explants were unchanged. An increase in cytokinin concentration led to formation of callus, which produced shoots which eventually produced flowers. The ability of yucca mutant tissues to proliferate and differentiate in an auxin-free medium indicates that yucca produces more endogenous auxin than the wild type.

EXAMPLE 7

Double mutant with YUCCA and an auxin reporter gene. As a genetic test of whether yucca has an increased level of physiologically effective endogenous auxin, a yucca/DR5-GUS double mutant was created that overexpressed YUCCA in the presence of the auxin reporter gene, a construct consisting of a highly active synthetic auxin response element referred to as DR5 (Ulmasov et al., *Plant Cell* (1997) 9:1963; Sabatini et al., *Cell* (1999) 99: 463) fused to the β-glucuronidase (GUS) reporter gene. Expression was detected by staining for GUS enzymatic activity. The auxin-reporter gene was much more active in the yucca mutants than in wild type plants transformed only with the DR5-GUS reporter construct.

EXAMPLE 8

Effect on the yucca phenotype of reducing free auxin levels: YUC/IAAL double mutant. If the yucca phenotype is caused by elevated levels of free auxin (IAA), it should be possible to suppress the yucca phenotype by reducing free auxin levels. The bacterial iaaL gene encodes an enzyme that conjugates free IAA to lysine, thereby reducing the levels of free auxin that are physiologically available by inactivating IAA. (Romano et al., *Genes Dev* (1991) 5:438) A double mutant expressing both iaaL and YUCCA, was created to determine the interaction between mutations at two sites. When iaaL is constitutively expressed in transgenic Arabidopsis using the 35S promoter, the pool of free IAA is reduced, which leads to decreased apical dominance (Romano et al., supra). In the YUC/iaaL double mutant, overexpression of iaaL masked the adult yucca phenotype, including suppression of the elongated hypocotyl and distinctive leave shape.

EXAMPLE 8

Effect of YUCCA overexpression in *E. coli* on detectable FMO activity. To test the enzymatic activity of the YUCCA gene product, YUCCA (SEQ ID NO. 1) was transformed into an *E. coli* overexpression vector pMalC2 and the recombinant YUCCA gene product was recovered, using the method of Brunelle et al., (*Drug Metab Dispos* (1997) 25:1001). For activity assays, the recombinant YUCCA gene product was incubated with 2 mM tryptamine, 1 mM NADP$^+$, 1 mM glucose-6-phosphate, and glucose-6-phosphate dehydrogenase at 37° C. Reactions were stopped by adding an equal volume of methanol. Substrate and products were separated by thin-layer-chromatography (TLC) with $CH_2CL_2$/methanol/TEA (75:20:5). The product was eluted from TLC plates and mass spectroscopy was performed to determine the molecular mass of the product. When tryptamine was used in vitro as a substrate for the recombinant YUCCA gene product, the reaction product had a fragmenation pattern by mass spectroscopy that was consistent with the pattern of N-hydroxyl tryptamine. These results indicated that the YUCCA gene product had NADPH oxidase activity and was able to convert tryptamine to N-hydroxyl tryptamine.

EXAMPLE 9

Overexpression of YUCCA homologs in Arabidopsis. To test whether the proteins encoded by homologs of YUCCA have similar functions in vivo and produce the yucca phenotype, two homologs were overexpressed as described above. The YUCCA2 protein (GenBank Accession CAB41936) having 53% amino acid sequence identity with YUCCA was overexpressed in Arabidopsis using the YUCCA2 coding sequence derived from a BAC clone (GenBank Accession ATF17N18). The YUCCA2 coding sequence was linked to its own promoter region, and CaMV 35S enhancers. This gene was transformed into Arabidopsis using techniques for transformation, selection, and regeneration similar to those described above. Plants overexpressing the YUCCA2 protein were found to have phenotypes identical to the original yucca mutant phenotypes, thus confirming that YUCCA2 protein is a FMO.

Two other yucca-like Arabidopsis mutants were isolated after activation tagging, and both were determined to be overexpressing the YUCCA3 protein (Genbank Accession Number AAB80641) which has 51% amino acid sequence homology to YUCCA. This result confirms that overexpressing the YUCCA gene, or its homologs, leads to the yucca phenotype.

EXAMPLE 10

Effects of YUCCA overexpression in the PHYA211 knockout background. The interaction between YUCCA and photoreceptor mutants was determined by overexpressing YUCCA in an Arabidopsis mutant known as phya211, which has a knockout in the PHYA211 gene. PHYA211 knockout Arabidopsis was transformed with an activation vector pSK1015 (Weigel et al., *Plant Physiol* (2000) 122:1003) containing the YUCCA gene and a CaMV 35S enhancer. The resulting yucca/phya211 mutatn plants were grown in white light, red light, far-red light, and blue light, and their hypocotyl lengths were measures. Plants of the yucca/phya211 double mutant were taller than phya211 mutants in white light, far-red light, and blue light.

EXAMPLE 11

Screening for suppressors and enhancers of the yucca mutant. The effects of suppressing YUCCA expression are determined by suppression screening, using techniques described by Weigel et al. (*Plant Physiol* (2000) 122:1003).

Screening for dominant suppressors is carried out at the T1 stage and screening for insertional (loss of function) mutants is carried out at the T2 stage. The T-DNA-tagged suppressor and/or enhancer genes identified by this method are then cloned and sequenced. Suppressors of the yucca mutant phenotype are found in auxin biosynthesis pathways or auxin signaling pathways.

EXAMPLE 12

YUCCA-induced gene expression. Micro-array experiments are performed to find out which genes are up or down regulated by YUCCA overexpression in the yucca mutant, using techniques described by Schena, et al., (*Science* (1995) 270:467). Total RNA and protein from the yucca mutants are isolated and compared to wild-type to identify those genes and proteins that have been up and/or down regulated using a micro-array strategy.

EXAMPLE 13

YUC/TIR3 double mutant. A double mutant with TIR3 and YUCCA is created to determine the contribution of each mutation to a phenotype, and to determine the interaction between mutations at two sites. TIR3 is a mutant having defects in auxin polar transport, giving rise to the Tir3 phenotype. (Reugger, *Plant Cell* (1997) 9:745).

Transforming Arabidopsis with TIR3 and with YUCCA (YUC), and obtaining enhanced YUCCA expression in the YUC/TIR3 double mutant, results in partial rescue of the Tir3 phenotypes. The club root is observed in the double mutant in the absence of NPA treatment. The $F_1$ generation displays delayed growth when compared to the wild-type plants.

EXAMPLE 14

YUC/EIR1 double mutant. A double mutant with EIR1 and YUCCA (YUC/IAAL) is created to determine the contribution of each mutation to a phenotype, and to determine the interaction between mutations at two sites. The EIR1 gene encodes an auxin influx carrier. (Luschnig et al., *Cell* (1998) 85:183). Mutations in both the E1R1 and YUC genes results in an expanded root system. The first generation of YUC/EIR1 double mutants resemble the yucca mutants, but are developmentally delayed.

EXAMPLE 15

YUC/YUC2 double knock-out mutant. A double mutant with knockout-outs in both the YUC2 and YUCCA genes is created to determine the contribution of each knock-out mutation to phenotype, and to determine interaction between the genes. The single knock-out mutants of both YUCCA and its closest homolog YUCCA2 do not have obvious phenotypes. The double knock-out mutant for both genes has some characteristics of auxin-deficient phenotypes.

EXAMPLE 16

Constitutive overexpression of YUCCA. In order to determine the effect of constitutive overexpression of the YUCCA gene, Arabidopsis is transformed with a construct that leads to constitutive overexpression. Removing the endogenous YUCCA promoter and inserting the CaMV 35S promoter into a YUC-containing expression vector elicits constitutive overexpression of YUCCA in plants transformed with this vector.

EXAMPLE 17

YUC/PHYB double mutant and YUC/PHYBPHYA. The YUC/PHYB and the YUC/PHYBPHYA double mutants are used to explore the specificity of the YUC interaction with photoreceptors. When expression of YUCCA is enhanced, YUCCA acts as a PHYA211 enhancer.

EXAMPLE 18

Method of enhancing a trait by altering YUCCA gene expression. Altering the expression of the YUCCA gene can enhance at least one trait in a plant. Plants having modified expression of the YUCCA gene are generated by transforming Arabidopsis with a construct containing YUCCA under control of a light-regulated promoter, using techniques described above. Exposure of the transgenic plant to light stimulates overexpression of YUCCA. Enhanced traits are measured, including enhanced production of FMO enzymes, increased hypocotyl length, increased root thickness, increased lateral root initiation, and increased apical dominance.

EXAMPLE 19

Method of identifying steps of auxin biosynthesis. Steps of auxin biosynthesis are determined by transforming Arabidopsis with a construct containing YUCCA and a suitable promoter, and carrying out suppression screening using the technique of Weigel et al. (*Plant Physiol* (2000) 122:1003) as described above. Following screening, auxin biosynthesis is determined by measurement of free IAA levels and/or by incorporation of labeled auxin precursors. Plants showing altered auxin biosynthesis are analyzed further to identify the gene tagged during the suppression screen.

EXAMPLE 20

Method for identifying steps of signal transduction pathways. Steps of signal transduction pathways can be identified by suppressing YUCCA expression and examining collateral effects on signal transduction. Arabidopsis is transformed with a construct containing YUCCA and a suitable promoter, and suppression screening is carried out using the technique of Weigel et al. (*Plant Physiol* (2000) 122:1003) as described above. Following suppression screening, plants having suppressed YUCCA expression are then examined for changes in their response to ethylene, including effects on ethylene-induced gene expression. Plants showing altered ethylene signal transduction are analyzed to identify the gene tagged during the suppression screen. The function of the tagged gene identifies a step in the ethylene signal transduction pathway.

EXAMPLE 21

Method for identifying a plant growth regulator. Plant growth regulators are identified by exposing substrate molecules to the action of AT-FMOs of the present invention and then measuring their ability to elicit the same effects as plant growth regulators. For example, tryptamine is mixed with AT-FMO produced by *Arabidopsis thaliana* cells overexpressing the YUCCA gene, resulting in the conversion of tryptamine to N-hydroxyl tryptamine. N-hydroxyl tryptamine is applied to a developing strawberry fruit. Auxin-like effects on fruit development, and selective activation of auxin-induced genes is observed as a result of treatment with N-hydroxyl tryptamine.

EXAMPLE 22

Method of studying interaction between plant growth regulators. Plants having altered YUCCA expression are used to identify and characterize interactions between plant growth regulators. Arabidopsis overexpressing the YUCCA gene is generated as described above, where the tissues contain 50% higher levels of endogenous IAA (auxin), also as described above. The level of auxin-induced gene expression is measured in YUCCA-overexpressing Arabidopsis. These plants are then exposed to 10 ppm ethylene, and the levels of both auxin-induced gene expression and ethylene-induced gene expression are measured.

EXAMPLE 23

Method of altered root development. Altered expression of YUCCA is useful as a method for altering root development. Arabidopsis is transformed with a construct containing YUCCA and a chemically-induced promoter as described above. Plants containing the inducible YUCCA construct are grown for three weeks on medium lacking the inducer, and various indicia of root development are measured including root length, root diameter, root morphology, rate of elongation, root hair development, lateral root initiation, anthocyanin content, and root orientation. Plants are transferred to fresh growth media, where half of the plants are transferred to medium lacking the inducer, and the other half of the plants are transferred to growth medium containing the inducer, which triggers overexpression of YUCCA. After one week of growth, indicia of root development are measured in both induced and noninduced plants. Roots of induced plants have a thicker and shorter primary root, and have more and longer root hairs than those of non-induced plants.

EXAMPLE 24

Screening method to identify FMOs. Homologs of YUCCA can be used in a screening method wherein inducing the yucca phenotype indicates that the homolog encodes a FMO. Homologs of the YUCCA gene are identified having at least 35% sequence identity to the nucleotide sequence of SEQ ID NO. 1. In the present example, a YUCCA homolog being screened is placed under control of a constitutively active promoter to induce constitutive overexpression of the homolog. YUCCA homologs are screened as follows to identify FMOs: 1) the coding sequence of the homolog being screened is operably linked to the CaMV 35S promoter to produce a functional expression vector; 2) the expression vector is introduced into an Arabidopsis host cell; 3) enhanced expression of the homolog is confirmed in transformed cells; 4) transformed plants are regenerated from transformed cells; 5) the phenotype of the transformed plants overexpressing the YUCCA homolog is measured. A homolog is considered to encode a FMO if altered expression of the homolog in Arabidopsis results in a phenotype resembling the yucca mutant phenotype described above.

EXAMPLE 25

Identifying xenobiotics. The oxidizing activity of the FMO encoded by the YUCCA gene is utilized to identify xenobiotic compounds in a sample. A method for identifying xenobiotics includes the steps of: 1) exposing a xenobiotic compound to the FMO encoded by the YUCCA gene; and 2) measuring the oxidized xenobiotic. From the identity of the oxidized xenobiotic, the identity of the xenobiotic compound originally present in the sample is determined. Enzymatically active FMO is recovered by lysing *E. coli* transformed to overexpress the YUCCA gene, as described above. A sample mixture is exposed to the YUCCA-encoded FMO, and formation of the compound benzydamine N-oxide is measured by HPLC and fluorometry as described by Ubeaud et al. (*Eur J Pharm Sci* (1999) 8: 255). Benzydamine is identified in the original sample by detecting the formation of benzydamine N-oxide after exposure to FMO.

EXAMPLE 26

Detoxifying xenobiotics. The oxidizing activity of the FMO encoded by the YUCCA gene is used to detoxify xenobiotics. The method for detoxifying xenobiotics includes the steps of exposing a xenobiotic to the FMO encoded by the YUCCA gene and measuring the toxicity of the oxidized xenobiotic. A sample containing benzydamine is exposed to the FMO encoded by the YUCCA gene, leading to formation of benzydamine N-oxide, as described above. Toxicity of the xenobiotic is measured by examining the effects of the sample containing benzydamine N-oxide on a test mammal., and comparing the effects of benzydamine N-oxide with the effects of an equivalent amount of sample containing benzydamine.

EXAMPLE 27

Screening method to identify FMO inhibitors. Inhibitors of FMOs can be identified by screening compounds for their ability to inhibit FMOs. Enzymatically active FMO is recovered by lysing *E. coli* transformed to overexpress the YUCCA gene, as described above. FMO activity is measured using thin-layer chromatography to quantitate the formation of the oxidized form of a known radiolabelled FMO substrate, as described by Cashman (*Anal Biochem* (1987)160: 294). A decrease in FMO activity following exposure to a compound indicates that a compound is a potential FMO inhibitor. When a potential FMO inhibitor is detected, further analysis is carried to determine whether the FMO inhibitor competes with the labeled substrate at the active site, or whether the FMO inhibitor acts directly on the FMO molecule.

EXAMPLE 28

Transforming the YUCCA gene into tobacco plants. To confirm that overexpression of FMOs in other plants leads to the yucca phenotype, the YUCCA gene was transformed and overexpressed in tobacco using the method described by Gallois et al. (*Methods Mol Biol* (1995) 49:39). The transgenic tobacco plants were found to have a dramatic change in phenotype, including long, narrow, epinastic leaves, identical to the phenotypes observed in Arabidopsis.

What is claimed is:

1. A method of enhancing at least one trait in a plant comprising:
  a) transforming a plant with an expression vector comprising a nucleotide sequence encoding a flavin-containing monooxygenase having the nucleotide sequence of SEQ ID NO:1;
  b) expressing the monooxygenase; and
  c) measuring said at least one trait.

2. The method of claim 1, wherein said plant is a monocotyledonous or a dicotyledonous plant.

3. The method of claim 1, wherein said expression vector comprises a constitutive promoter.

4. The method of claim 1, wherein said expression vector comprises an inducible promoter.

5. The method of claim 1, wherein said expression vector comprises a light-regulated promoter.

6. The method of claim 1, wherein said plant is tobacco or *Arabidopsis thaliana*.

7. The method of claim 1, wherein said trait is increased hypotcotyl elongation.

8. The method of claim 1, wherein said trait is increased root thickness.

9. The method of claim 1, wherein said trait is increased root hair development.

10. The method of claim 1, wherein said trait is increased lateral root initiation.

11. The method of claim 1, wherein said trait is increased apical dominance.

12. The method of claim 1, wherein said trait comprises epinastic leaf growth.

13. The method of claim 1, wherein said trait is increased levels of endogenous auxin.

14. A method of increasing auxin levels in a plant, comprising:
  a) transforming a plant with an expression vector comprising a nucleotide sequence encoding a flavin-containing monooxygenase having the amino acid sequence of SEQ ID NO:2; and
  b) expressing the mono oxygenase in the plant.

15. The method of claim 14, wherein said plant is an *Arabidopsis thaliana* or a tobacco plant.

16. The method of claim 14, wherein said expression vector comprises a light-regulated promoter.

17. A method of increasing the growth and yield of a plant, comprising:
  a) transforming a plant with an expression vector comprising a nucleotide sequence encoding a *Arabidopsis thaliana* flavin-containing monooxygenase having the amino acid sequence of SEQ ID NO:2; and
  b) expressing the monooxygenase in the plant.

18. The method of claim 17, wherein said plant is *Arabidopsis thaliana*.

19. The method of claim 17, wherein said plant is a tobacco plant.

20. The method of claim 17, wherein said expression vector comprises a light-regulated promoter.

21. A transgenic plant produced by a method comprising:
  a) transforming a plant with an expression vector comprising a nucleotide sequence encoding a *Arabidopsis thaliana* flavin-containing monooxygenase having the amino acid sequence of SEQ ID NO:2; and
  b) expressing the monooxygenase in the plant.

22. The plant of claim 21, wherein said plant is *Arabidopsis thaliana*.

23. The plant of claim 21, wherein said plant is a tobacco plant.

24. The plant of claim 21, wherein said expression vector comprises a light-regulated promoter.

25. A transgenic plant having increased growth characteristics, wherein said transgenic plant comprises a recombinant expression vector that expresses a flavin-containing monooxygenase having the amino acid sequence of SEQ ID NO:2.

26. The plant of claim 25, wherein said plant is *Arabidopsis thaliana*.

27. The plant of claim 25, wherein said plant is a tobacco plant.

28. The plant of claim 25, wherein said expression vector comprises a light-regulated promoter.

29. The plant of claim 25, wherein said plant also comprises increased root growth characteristics.

30. A seed derived from the transgenic plant of claim 25, wherein said seed comprises a recombinant expression vector that expresses a flavin-containing monooxygenase having the amino acid sequence of SEQ ID NO:2.

31. A method of increasing root development in a plant comprising:
  a) transforming a plant with an expression vector comprising a nucleotide sequence encoding a flavin-containing monooxygenase having the amino acid sequence of SEQ ID NO:2; and
  b) expressing the monooxygenase in said plant, wherein said expression leads to an increased root development.

32. The method of claim 31, wherein said increase root development is selected from the group consisting of increased: root length, root diameter, rate of elongation root hair development, and anthocyanin content.

33. The method of claim 31, wherein said plant is *Arabidopsis thaliana*.

34. The method of claim 31, wherein said plant is a tobacco plant.

35. The method of claim 31, wherein said expression vector comprises a light-regulated expression vector.

* * * * *